(12) United States Patent
Donovan

(10) Patent No.: US 7,481,006 B2
(45) Date of Patent: Jan. 27, 2009

(54) OUTER AND INNER EAR DRYING SYSTEM

(76) Inventor: Stephen Donovan, 1053 Field Ave., Plainfield, NJ (US) 07061

( * ) Notice: Subject to any disclaimer, the term of this patent is extended or adjusted under 35 U.S.C. 154(b) by 343 days.

(21) Appl. No.: 11/222,397

(22) Filed: Sep. 8, 2005

(65) Prior Publication Data

US 2007/0051008 A1 Mar. 8, 2007

(51) Int. Cl.
*F26B 21/04* (2006.01)
(52) U.S. Cl. .................. 34/218; 34/90; 34/99; 392/380
(58) Field of Classification Search .................. 34/218, 34/224, 174, 90, 96–99; 392/380; 381/328, 381/370, 374; 181/130, 135
See application file for complete search history.

(56) References Cited

U.S. PATENT DOCUMENTS

| 4,287,673 | A | * | 9/1981 | Wolter ............................ 34/97 |
| 4,391,047 | A | * | 7/1983 | Janssens et al. ................ 34/97 |
| 5,067,444 | A | | 11/1991 | Parker ......................... 119/85 |
| 5,979,072 | A | | 11/1999 | Collins, II ....................... 34/90 |
| 5,987,771 | A | | 11/1999 | Curtin ............................. 34/97 |
| 6,059,803 | A | | 5/2000 | Spilman ...................... 606/162 |
| 6,599,297 | B1 | | 7/2003 | Carlsson et al. ............. 606/109 |
| 6,725,568 | B2 | | 4/2004 | Gronka ........................ 34/437 |
| 6,739,071 | B2 | | 5/2004 | Andis et al. ..................... 34/96 |
| 2004/0083620 | A1 | | 5/2004 | McCambridge ................ 34/96 |

* cited by examiner

*Primary Examiner*—Kenneth B Rinehart
(74) *Attorney, Agent, or Firm*—Ernest D. Buff & Associates LLC; Ernest D. Buff; Harry Anagnastopoulos

(57) ABSTRACT

A system dries water droplets within a person's outer and inner ear. The presence of the droplets is typically caused by swimming, showering, bathing, and other activities associated with water sports such as diving, water polo and the like. A hair dryer blows warm air at a distance into a handheld drying apparatus. One or more diffusion chambers containing a plurality of apertures deliver warm air from the hair dryer into the outer ear. An integral central tubular element forming part of the diffusion chamber delivers warm air from the hair dryer into the inner canal. The diffusion chamber has a handle to help position the central tubular element within the inner ear canal. The distance between the hair dryer and the handheld drying apparatus may be varied to select a comfortable warmth level and warm air velocity.

3 Claims, 2 Drawing Sheets

OUTER AND INNER EAR DRYING SYSTEM

BACKGROUND OF THE INVENTION

1. Field of the Invention

The present invention relates to a system for drying the outer and inner ear of a person, such as a swimmer or the like, to remove water that has entered the ear canal or has potential to enter the ear canal.

2. Description of the Prior Art

Many patents address issues related to drying water in a swimmer's ear, since water accumulation has the potential to upset balance and cause ear infections. Representative patents and patent publications that relate to drying of water in the ear canal are discussed hereinafter.

U.S. Pat. No. 5,067,444 to Parker (hereinafter, the "'444 patent") discloses a hand-held apparatus for grooming animals. The hand-held animal grooming apparatus is configured as a currycomb with a sealed upper edge and serrated lower edge generally formed as a circular hoop, and further comprises a handle with an axial passage to a flexible conduit fed by a hot air blower. When the currycomb is in use against the body of the animal, the open face is effectively sealed by the animal's body, and warm air is blown along the serration to dry the animal during the combing operation. Alternative versions of the instrument include hollow-chamber brushes having similar handles and having a plurality of air passages for directing heated airflow into the handle and out of these passages, generally along the bristle directions. The apparatus disclosed by the '444 patent cannot be utilized for drying moisture from the outer and inner ear. The direct connection of heated air to the grooming device brings very hot air directed at a high velocity over a large area. This feature can result in damage to the delicate anatomical structure of inner ear.

U.S. Pat. No. 5,979,072 to Collins, II discloses an external auditory canal drying apparatus. The external ear canal drying apparatus comprises a housing unit, a forced air generating unit with an exhaust outlet, and a nozzle adapter unit that is removably received in the exhaust outlet of the forced air-generating unit. The forced air-generating unit includes an air inlet and exhaust conduit that is operatively associated with a blower motor and a heating element to deliver heated forced air through the exhaust port of the forced air-generating unit. The nozzle adapter unit includes a soft pliable tapered housing that is dimensioned to be partially received in a person's ear canal. In one version, the tapered housing is further provided with a suspended central conduit that delivers the heated air to the person's inner ear. Furthermore, the central conduit also defines a concentric return passageway arranged within the tapered housing to allow the heated air to be vented from the person's ear canal. In another version of the '072 patent device, the exterior of the tapered housing is provided with fluted recesses, through which the heated air escapes. Given the sensitive nature of the human ear, both the air speed generated by the blower motor and the air temperature generated by the heating element must be maintained at fairly low values such that the air flow capacity of the blower motor will not exceed 10 cc/sec and the temperature of the heating element will not exceed 39° C. The blower motor must also have a very low decibel rating given its use in close proximity to a user's ear. However, no means for obtaining these parameters are discussed, since the blower air output is directly exhausted into the inner ear. The airflow from the blower to the inner ear is fixed. Consequently, it cannot be adjusted according to the comfort level desired by the user. No means are provided for drying moisture or water droplets in the outer ear. Moreover, since the apparatus inserted into the ear is an electrical device, there are shock hazards associated with the '072 patent device.

U.S. Pat. No. 5,987,771 to Curtin discloses a scent charged aeration capsule assembly for a hair blower. The scent charged aeration capsule assembly is adapted to be placed over the outlet end of a hair blower whereby, during the blower's operation, a selected fragrance may be directed into a subject's hair from a fragrance laden pad seated within a nozzle. The scented aeration capsule does not dry water in the ear canal. It instead blows aerated particles into the user's hair, and potentially onto the skin and even into the ear itself.

U.S. Pat. No. 6,059,803 to Spilman (hereinafter, the "'803 patent") discloses a portable hand held ear vacuum device. The portable hand held ear vacuum device has particular applications for removing fluid and debris from an ear canal. The ear vacuum device comprises a handle element with a motor linked to a fan and a control switch, and a collection chamber for collecting fluid and other debris from an ear canal. The collection chamber is secured to the handle element and has a reservoir therein for collecting and storing accumulated fluid and debris from the ear canal. An ear insertion element is secured to the collection chamber, and is provided with an aperture therein, the aperture being continuous with the reservoir in the collection chamber. The motor in the handle creates a vacuum within the collection chamber, enabling fluids and debris to be drawn from the ear canal into a detachable reservoir by suction. Suction is only possible, if and only if, the water droplets are free and are not wetted to the interior of the inner ear canal. The water droplets that enter the ear during swimming or surfing are forced, at high velocity, into the inner ear and are generally wetted. The '803 patent's ear vacuum apparatus does not evaporate the water droplets from a person's ear; rather the apparatus sucks the moisture and debris from the user's ear. Furthermore, there is also no means disclosed for drying the outer ear.

U.S. Pat. No. 6,599,297 to Carlsson, et al. (hereinafter, the "'297 patent") discloses a device for ventilating the middle ear. The middle ear ventilating device operates by means of a ventilation tube, which is made of a tissue-compatible material, preferably titanium. The ventilation tube has a through-channel for air communication between the cavity of the middle ear and the outside air. The device for ventilating the middle ear uses an implanted titanium ventilation tube, which connects the middle ear to the outside, thereby draining any fluids in the middle ear. The '297 patent's disclosure has nothing to do with removing moisture or water droplets from the inner ear canal and the outer ear due to water accumulation, primarily from showering, swimming, or water surfing, but instead discloses a drainage type apparatus to be utilized in connection with a medical condition for draining fluid out of the middle ear.

U.S. Pat. No. 6,725,568 to Gronka discloses an ear canal dryer and method of use thereof. The ear canal dryer comprises a bulb and a speculum, each having an air flow controller. The bulb has a ball check valve to force the air through the speculum, which also has a ball check valve. By inserting the speculum into the ear canal and squeezing the bulb, an air stream is injected into the ear canal causing evaporation of fluid and carrying the moisture out of the canal. The speculum has an external airflow director in the form of grooves for directing air inside the cavity and out along the outer surface of the speculum. The device pulls room air into the ear canal through a tapered speculum. The moist air is prevented from entering the bulb by use of ball check valves. External grooves on the tapered speculum allow moist air to escape to the ambient, thereby drying any moisture or water droplets in the ear canal. The squeezing of the bulb can produce very high velocity air through the ear canal, especially if the bulb is squeezed at a fast rate, risking injury to the delicate eardrum. Since the air delivered into the inner ear is ambient air, it is at room temperature and any drying action is slow. Drying of moisture in the inner ear is impossible when the room's humidity is high.

U.S. Pat. No. 6,739,071 to Andis, et al. (hereinafter, the "'071 patent") discloses a combined diffuser and concentrator for a hair dryer. The combined diffuser and concentrator includes a handle, a body connected to the handle portion, a barrel connected to the body portion having an inner member defining a first air passageway, an outer member slidably coupled to the inner member and defining a second air passageway that is substantially parallel to the first air passageway, and a shutter. The shutter is coupled to the inner member and is movable in response to sliding of the outer member with respect to the inner member to selectively direct air through the first air passageway and the second air passageway. The outer member is slidable with respect to the inner member from a first position wherein air flows through only the first passageway providing a concentrated airflow. In a second position air flows through the second air passageway, thereby providing a diffuse airflow. The hair dryer combines a diffuser and concentrator assembly. The '071 disclosure has nothing to do with drying moisture or water droplets in the inner ear or outer ear.

U.S. Patent Application No. 2004/0083620 to McCambridge, et al. discloses an attachment for a handheld dryer. The disclosed attachment includes a shell and a dryer barrel-receiving portion. The barrel-receiving portion comprises a plurality of spaced apart elongated fins connected to a shell and configured for frictionally receiving a dryer barrel. The shell has a larger diameter compared to the barrel. A first passage is defined between the shell and the dryer and terminates in a shell inlet defined between the shell and the dryer barrel. The patent publication discloses an attachment to be utilized in conjunction with a handheld dryer. The barrel of the hair dryer is attached to a nozzle, thereby increasing the velocity of the airflow. A concentric annular shell with fins is attached to the barrel of the hair dryer, creating a mixing region between the nozzle flow air and the air sucked between the shell and the barrel by the Venturi effect. The increase volume of flow provides a higher flow capacity from the hair dryer without using a larger blower within the hair dryer. The patent application disclosure has nothing to do with drying moisture or water droplets within inner ear or outer ear. It merely increases the volumetric air output from a hair dryer, but drastically decreases the temperature and velocity of air delivered from the hair dryer; both factors decrease any moisture drying action.

There remains a need in the art for a drying system that effectively dries water in the inner ear canal caused by swimming and participation in water based sports including diving and water surfing. Not only does water present in the inner ear canal need to be removed, but water in the outer ear must also be removed since movement of the head may permit water droplets from the outer ear to enter the inner ear canal. The process of drying these water droplets requires delivery of warm air at a velocity and warmth sufficiently low that the sensitive anatomical structure of the ear is not affected.

SUMMARY OF THE INVENTION

The present invention provides a system for drying a person's outer and inner ear. The present invention is adapted for use by persons involved in water sports, or even for everyday use after showering, bathing, or washing one's face. Water typically enters the inner ear canal easily. If water is left within the inner ear for a prolonged period of time, several problems arise. Water in the inner ear can result in disorientation, discomfort and more serious problems, such as the risk of infections. Repeated water sports or activity only aggravate the problem. Water that is collected in the outer ear can also find its way into the inner ear causing additional problems. It is therefore desired to dry water accumulated in the outer and inner ear simultaneously to eliminate discomfort, restore balance and prevent the possibilities of ear infection.

The outer and inner ear drying system comprises a hand held dryer which is positioned at a distance from a handheld drying apparatus having one or more diffusion chambers and a central tubular element. The diffusion chambers have apertures designed to distribute warm air from the hair dryer effectively into the complex shape of the outer ear, thereby drying any water droplets present. The central cylindrical tube, located within the diffusion chamber, has a diameter sufficiently small to fit into the inner ear canal with a clearance and delivers warm air from the hair dryer into the inner ear canal, drying any water droplets present. The handheld drying apparatus has a handle that is permanently attached to the diffusion chamber and the handle is used to position the central tubular element within the inner ear canal. The diameters of the apertures in the diffusion chamber range from 0.005 to 0.030 inches. The diameter of the central tubular element is in the range of 0.030 to 0.070 inches. Since the hair dryer is located at a distance from the handheld drying apparatus, the velocity of warm air in the central tubular element is generally small and can be decreased at will by the user by placing the handheld drying apparatus further away from the blow dryer. The warmth of the air delivered also decreases when the distance between the hair dryer and the handheld drying apparatus is increased.

Significant advantages are realized by practice of the present invention. The key features of the outer inner ear drying device, which includes, in combination, the following features set forth below:

1) a hand held device without a motor, blower or any electrical connections comprising a diffusion chamber;

2) the diffusion chamber having an integrally attached central tubular element with an aperture, wherein the aperture has a diameter range of 0.030 inch to 0.070 inch;

3) the diffusion chamber having a number of apertures surrounding the central tubular element;

4) the central tubular element of the hand held device inserted into the inner ear canal;

5) the apertures surrounding the central tubular element are in close proximity and covering the outer ear;

6) a conventional hair dryer brought in close proximity with the diffusion chamber on the side distal from the central tubular element;

7) the warmed air from the conventional hair dryer entering the diffusion chamber and directing the warmed air into the inner ear through the central tubular element and to the outer ear through the apertures surrounding the central tubular element;

8) the user increasing or decreasing the distance between the conventional hair dryer and the hand held device so as to adjust the velocity of warm air entering the inner ear canal according to the user's convenience and preferences;

9) the warm air evaporating any moisture or water droplets present within the inner ear canal and the outer ear.

Advantageously, the velocity of warm air entering the inner ear canal is low due to the small aperture in the central tubular element in the diffusion chamber. The inner ear is thereby protected from exposure to a high velocity warm air stream.

BRIEF DESCRIPTION OF THE DRAWING

The invention will be more fully understood and further advantages will become apparent when reference is had to the following detailed description of the preferred embodiments of the invention and the accompanying drawing, in which.

DETAILED DESCRIPTION OF THE INVENTION

Figure 1:
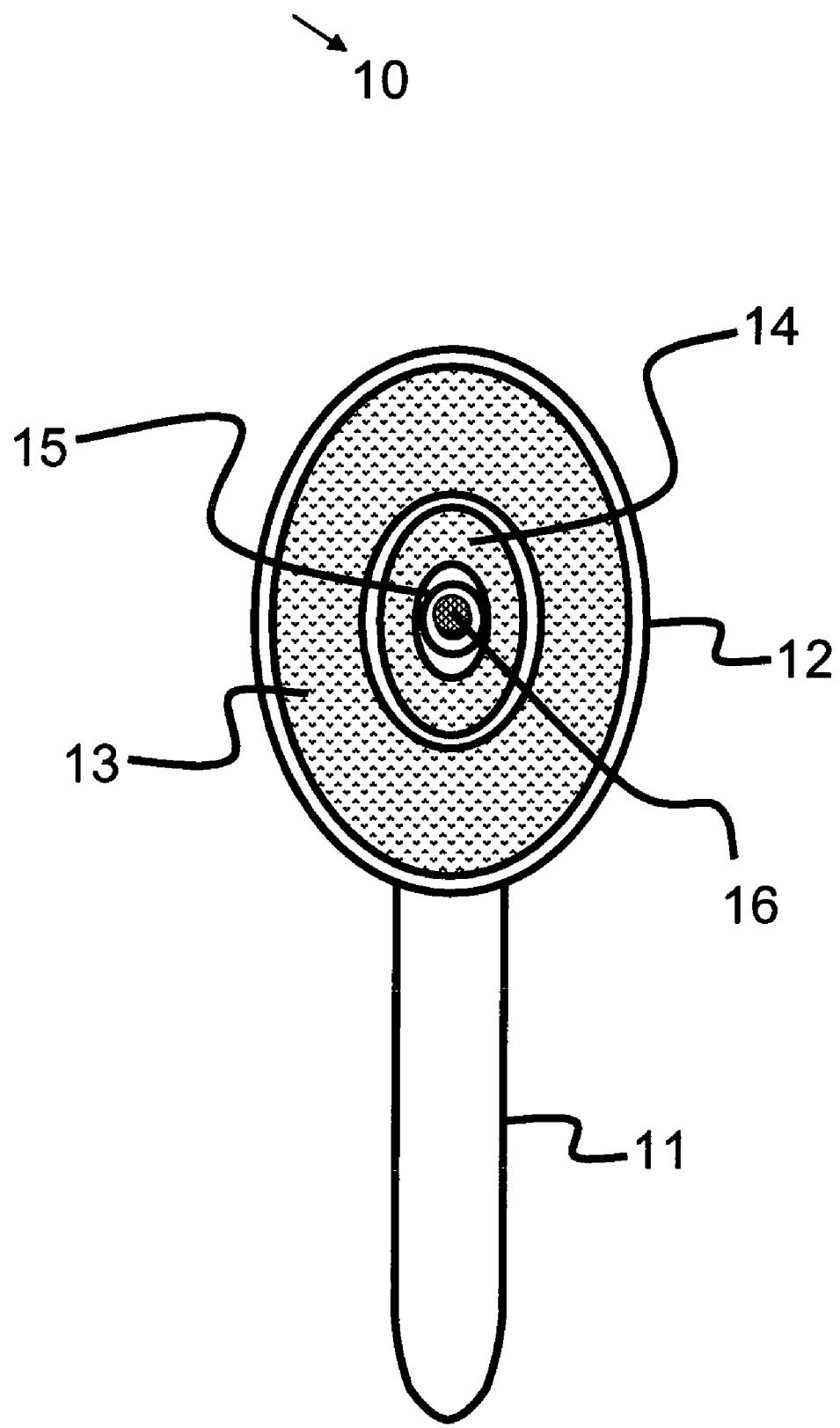
FIG. 1 is an aerial view of the Outer and Inner Ear Drying system.

Swimmers and surfers generally find it difficult to hear immediately after participating in water sports. On such occasions, salt water or chlorinated swimming pool water droplets tend to enter the outer and inner ear. The droplets of water, especially within the inner ear, are extremely annoying; the presence of the water frequently decreases the ability to hear. It also provides strange sensations, including disturbance of balance, which is related to proper functioning of the inner ear. If water within the inner ear is not promptly removed, it may result in an ear infection and lead to additional complications.

The outer and inner ear drying system of the present invention provides a handheld drying apparatus that functions, in combination with a hair dryer, to safely dry and remove water from a person's outer and inner ear. The system has particular applications in preventing ear infections resulting from moisture accumulation within the outer and inner ear portions, and has particular applications especially suited for swimmers, surfers, water polo players, and the like. Heated warm air is blown through the handheld drying apparatus, which provides diffusion of warm air and focuses the heated air into the outer and inner portions of the ear. The handheld drying apparatus broadly includes a handle portion, one or more diffusion chambers and a central tubular element. The handheld drying apparatus may be preferably provided with an outer and inner diffusion chamber to conform to the complex geometrical shape of the outer ear. Both outer and inner diffusion chambers have a number of small apertures, having a diameter typically ranging from 0.005 to 0.030 inches, for delivering warm air to the outer ear. Due to the small size of these apertures in the diffusion chambers, warm air is delivered to the complex shape of the outer ear and dries any water droplets present. The warm air entering the ear canal effectively dries any moisture present within the ear canal. The central tubular element typically has a diameter of 0.030 to 0.070 inches. All the elements of the hand held device are made from a heat resistant plastic material.

The key features of the design provide safe practice for drying water within the outer and inner ear. Since the hand held unit has no motor drive, there is no possibility of electrical hazards. Due to the small diameter of the aperture in the central tubular member, which is typically in the range of 0.030 to 0.070 inches, the overall air flow and the pressure generated within the inner ear is small. The warm airflow within the central tubular element, however, is sufficient to dry any water droplet present within the inner ear in a reasonable time, typically within a few minutes of usage of the device. The airflow through the apertures surrounding the central tubular member effectively dries any water droplets or moisture present in the outer ear. The user is free to manually move the hair dryer closer or further away from the hand held unit according to his or her individual comfort level.

During use, the central tubular element of the hand held device is placed within the inner ear canal and a hair dryer is placed in close proximity with the hand held device on a side opposed to the tubular element. Warm air is provided by a traditional hair dryer, which enters the inner ear through the central tubular element and dries any moisture or water droplets present within the inner ear. The apertures surrounding the central tubular element deliver warm air by diffusion to the outer ear, drying any moisture or water droplets present. The diffusion chamber is large enough to protect the side portions of the face from being exposed to warm heated air. Advantageously, drying the moisture accumulated within the inner ear and outer ear minimizes the possibility of moisture induced ear infections.

FIG. 1 illustrates a frontal view of the outer and inner ear-drying system, shown generally at 10. Handle 11 is attached to diffusion chamber 12. Diffusion chamber 12 is further comprised of a large outer diffusion section 13 and a smaller inner diffusion section 14, which is slightly raised from the outer diffusion section 13. The overall shapes of the outer and inner diffusion chambers, 13 and 14, respectively, provide warm air effectively to the complex shape of the outer ear. Inner conduit portion 16 is formed by way of a central tubular element, which is an elevated cylindrical portion 15, so that the cylindrical portion 15 is adapted to slide through the ear canal to deliver warm air through the inner conduit portion 16. The outer diffusion section 13 and inner diffusion section 14 contain a series of perforations or apertures that act to provide warm air to the outer ear. The inner conduit portion 16 acts to provide warm air into the inner ear.

Figure 2:
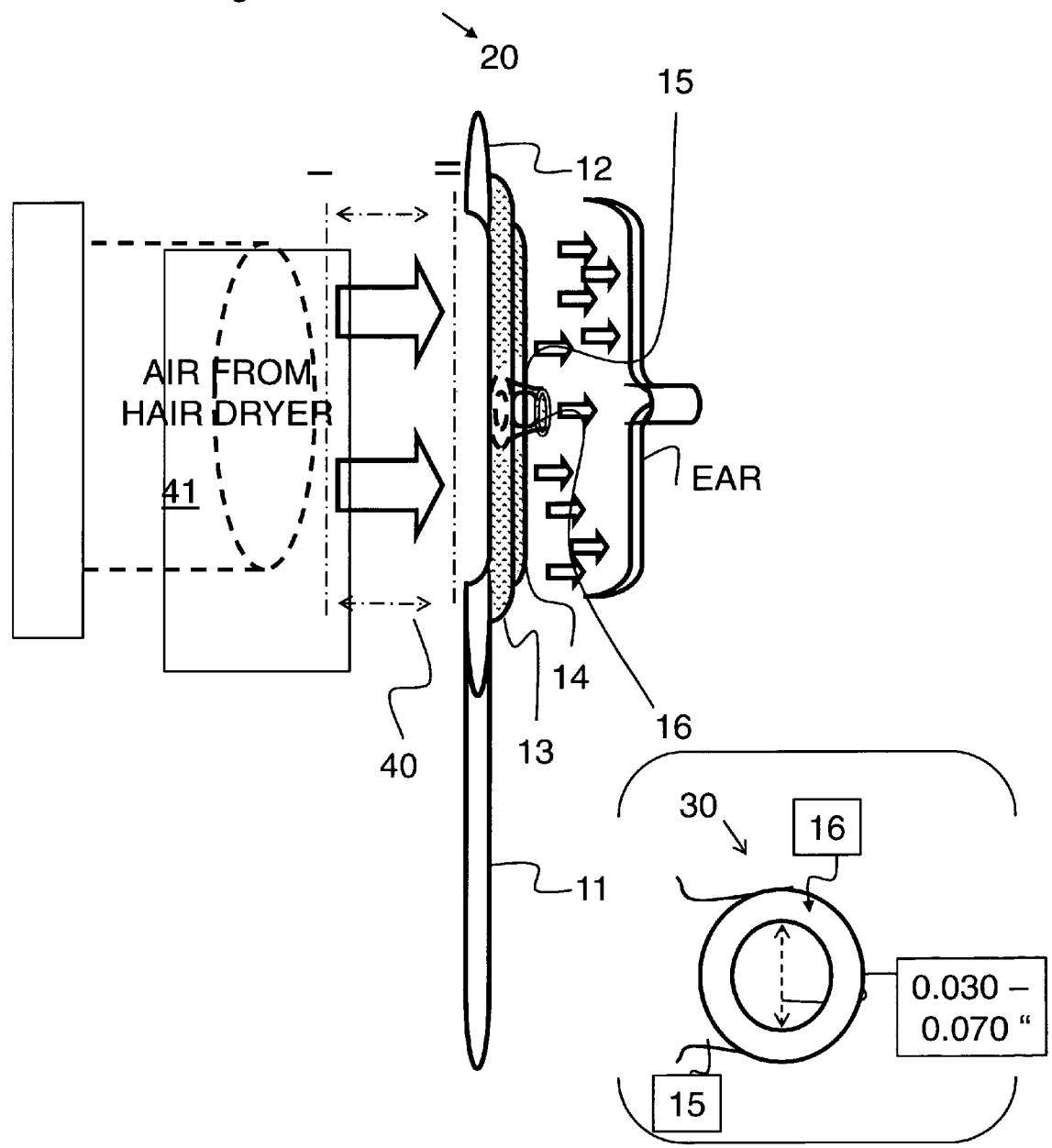
FIG. 2 is a side view of the Outer and Inner Ear Drying system showing the hair dryer and the handheld drying apparatus during use.

FIG. 2 shows, generally at 20, a side view of the outer and inner ear drying system when it is in use. Handle 11 is attached to diffusion chamber 12. Diffusion chamber 12 is curved in shape, so as to form a chamber for receiving air from a blow dryer 18. The outer diffusion section 13 is provided with a series of perforations in order to diffuse the entering air. Inner diffusion section 14 is also provided with a series of perforations or apertures for diffusion of airflow. The diffusion chambers 13 and 14 provide warm air to the complex geometrical shape of the outer ear through the apertures. Cylindrical portion 15 provides a channel for the warm air to flow directly into the conduit portion 16 and into the inner ear. The cylindrical portion 15 is inserted into the inner ear canal 17.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. An outer and inner ear drying system, comprising:
   a) a hair dryer directing warm air into a handheld drying apparatus;
   b) said handheld drying apparatus comprising:
      i) one outer diffusion chamber and one inner diffusion chamber, said inner and outer diffusion chambers conforming to the complex geometrical shape of the outer ear, and said diffusion chambers having a plurality of apertures with diameters ranging from 0.005 to 0.0030 inches;
      ii) a central tubular element having a diameter ranging from 0.030 to 0.070 inches integrally attached to said diffusion chamber;
      iii) a handle permanently attached to said diffusion chamber for holding said handheld drying apparatus so that said central tubular element is positioned within said inner ear canal and said central tubular element is positioned in close proximity with said outer ear;

wherein said diffusion chambers direct warm air form said hair dryer into an outer ear, and said central tubular element directs warm air from said hair dryer into an inner ear canal.

2. An outer and inner ear drying system as recited by claim 1, wherein said central tubular element enters said inner ear canal freely with a clearance.

3. An outer and inner ear drying system as recited by claim 1, wherein said handheld drying apparatus comprises a diffusion chamber and central tubular element and handle molded from a high temperature polymeric material.

* * * * *